United States Patent
Tan et al.

[11] Patent Number: 5,759,942
[45] Date of Patent: Jun. 2, 1998

[54] ION EXCHANGE RESIN CATALYST FOR THE SYNTHESIS OF BISPHENOLS AND THE PROCESS FOR PREPARING THE SAME

[75] Inventors: Qiu Tan; Zuquan Jin; Hongshou Jiang; Zongzhang Liu; Bingjun He, all of Tianjin, China

[73] Assignees: China Petro-Chemical Corporation, Beijing; Tianjin University, Tianjin, both of China

[21] Appl. No.: 546,710

[22] Filed: Oct. 23, 1995

[30] Foreign Application Priority Data

Oct. 25, 1994 [CN] China .................. 94117514.6

[51] Int. Cl.$^6$ .................................................. B01J 31/10
[52] U.S. Cl. ........................... 502/168; 502/155; 502/159
[58] Field of Search .............................. 502/155, 159, 502/168

[56] References Cited

U.S. PATENT DOCUMENTS 3,965,039  6/1976  Chaplits et al. .................. 252/426
4,820,740  4/1989  Li ........................................ 521/32
5,502,016  3/1996  Kiedik et al. ....................... 502/11

*Primary Examiner*—Glenn Caldarola
*Assistant Examiner*—Alexander G. Ghyka
*Attorney, Agent, or Firm*—Kane, Dalsimer, Sullivan, Kurucz, Levy, Eisele and Richard LLP

[57] ABSTRACT

An ion exchange resin catalyst containing sulfonated styrene-divinylbenzene copolymer, a porous structure with micropore area and transfer pass networks, the transfer pass network is composed of main pass networks and branch pass networks, in non-swollen state, the pore size of the main pass network is $9\times10^3$–$38\times10^3$ nanometer and the pore size of the branch pass network is 20–150 nanometer, the pore size of the micropore area pass is 5–20 nanometer, wherein the pore capacity of the micropore pass with the pore size of 5–10.4 nm is more than 50% of the total pore capacity of the micropore area, and the ratio of the pore capacity of the micropore area to that of the transfer network area is 0.25–1.1. The catalyst is useful to condense phenols with ketones.

12 Claims, 1 Drawing Sheet

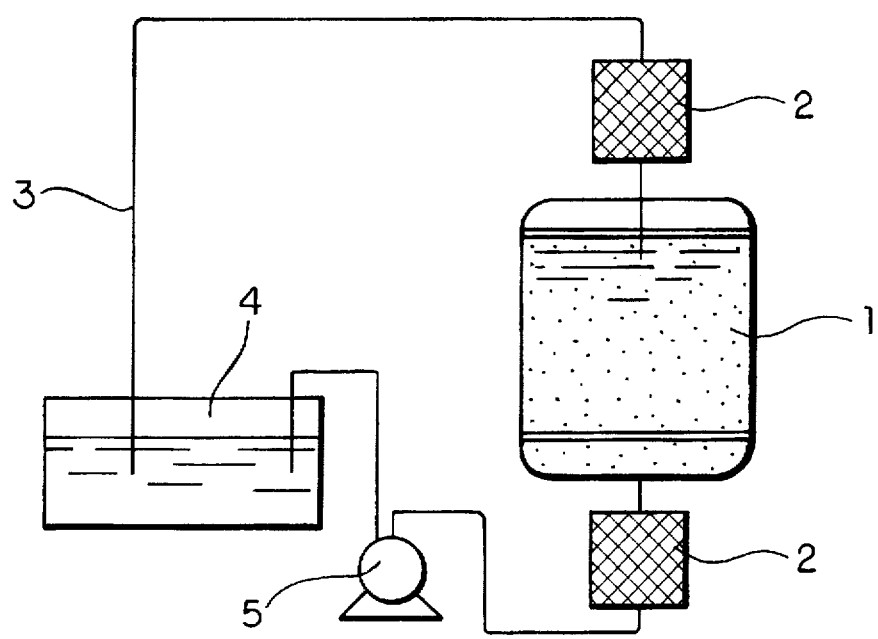

ION EXCHANGE RESIN CATALYST FOR THE SYNTHESIS OF BISPHENOLS AND THE PROCESS FOR PREPARING THE SAME

FIELD OF THE INVENTION

This invention relates to an ion exchange resin catalyst for the synthesis of bisphenols and the process for preparing the same, more particularly, this invention relates to a styrene-divinylbenzene series strong acidic cation exchange resin catalyst for the synthesis of bisphenols, and the process for preparing the same.

BACKGROUND OF THE ART

Recently, the base material used in the ion exchange resin catalysts is a gel type or macroreticular type sulfonic acid cation exchange resin with exchange capacity of at least 2.0 meq/g, preferably 3.0–5.5 meq/g dry resin, such as sulfonated styrene-divinylbenzene copolymers, sulfonated phenol-formaldehyde resins and sulfonated benezene-formaldehyde resins.

The commonly used method for modifying the above mentioned base material of ion exchange resin into catalysts used for the synthesis of bispenols comprises introducing cocatalytic group, such as mercapto group into the base material of ion exchange resin so as to increase its selectivity and reaction velocity. In the case of introducing mercapto group, there are reported many processes in literature, such as partial reduction method (U.S. Pat. No. 3,172,916), partial esterification method (U.S. Pat. No. 3,153,001; BP 937,072) covalence bonding method through sulfonamide (U.S. Pat. Nos. 4,294,995, 4,346,247, 4,396,728) and partial neutralization method.

As the catalyst obtained by partial neutralization method has better catalytic performances than those obtained by other methods, i.e. higher recovery and purity of product bisphenol, the partial neutralization method has been paid more attention, and partial neutralization methods using various mercapto group-containing compounds have successively been developed. These mercapto group-containing compounds (mercaptolizing agent) are: tetrahydrothiazole or thiazolidine (U.S. Pat. Nos. 3,634,341, 3,760,006), aryl mercaptoamine or its salts (U.S. Pat No. 4,045,379), pyridylalkylthiol (U.S. Pat. No. 4,478,956), N-(2-mercapto alkyl) amide (U.S. Pat. No. 4,595,704; CN 85106111), polymercaptoalkylamine (EP 268,318; U.S. Pat. No. 4,820,740), N-alkylmercaptoamine (EP 144,735) and alkylmercaptoamine (U.S. Pat. No. 3,394,089; BP 1,183,564), and the like.

Although in the above mentioned prior art, various co-catalytic groups with different molecular structures, and the corresponding methods for introducing these groups into the fundamental resin backbone have been developed, and these techniques do increase the selectivity and activity of the catalysts to some extent, as these techniques are only limited to the change and transform in species of the co-catalytic groups and methods for introducing them, and do not relate to the fundamental resin itself, the increase in selectivity and activity of the catalysts is limited. For example, in the case of using modified resin catalyst in the condensation reaction between phenol and acetone, the conversion of acetone to bisphenol A is lower then 50%, the selectivity to product p,p-bisphenol A is less then 96%, and the color index is as high as 40–50. Even by using a modification method disclosed by this inventors in Chinese Patent Application No. 91108831.8, the conversion of acetone can reach 53%, and the selectivity to product p,p-bisphenol A can reach 99.23%, but the color index of the product is still higher than 20.

SUMMARY OF THE INVENTION

The object of this invention is to provide an ion exchange resin catalyst with special structure for use in synthesizing high quality p,p-bisphenol A (hereinafter refered to "bisphenol A").

Another object of this invention is to provide a process for the preparation of this catalyst.

DETAILED DESCRIPTION OF THE INVENTION

The ion exchange resin catalyst according to the invention comprises a sulfonated styrene-divinylbenezene copolymer, the exchange capacity of which is 2.8–5.5 meq/g dry resin, and 10–30% of the sulfonic acid groups of which are linked to the alkylmercaptoamine having 1–7 carbon atoms through an ionic linkage of ammonium sulfonate. This catalyst has a porous structure containing micropore areas and transfer pass networks, the transfer pass network being composed of main pass networks and branch pass networks. In non-swollen state, the pore size of a main pass network is $9 \times 10^3 - 38 \times 10^3$ nanometer, the pore size of a branch pass network is 20–150 nanometer; and the pore size of a micropore area pass is 5–20 nanometer, wherein the pore capacity of the micropore pass with a pore size of 5–10.4 nanometer is more than 50% of the total pore capacity of the micropore areas, and the ratio of the pore capacity of the micropore areas to that of the transfer network areas is 0.25–1.1.

The ion exchange resin catalyst of the present invention with the above-mentioned special structure and having high activity and high selectivity is prepared by the following steps:

(1) Suspension polymerizing to prepare small resin beads

Monomers of styrene and divinylbenzene are suspension polymerized in the presence of a pore-forming agent. The weight ratio of divinylbenzene to styrene is 5–25%:75–95%, preferably 8–15%:85–92%. The pore-forming agent is composed of a refined paraffin wax with melting point of 54°–62° C. and NY-200# petroleum spirit with the ratio of parraffin wax to petroleum spirit being 1:3–6.1. The amount of the pore-forming agent used is to enable the monomer: the pore-forming agent= 60–80%:20–40% (by weight). The amount of water added is about 3–5 fold, preferably about 4 fold by weight of the monomer. The temperature of the polymerization is about 60°–95° C., preferably 80°–90° C. The polymerization is preferably carried out in two stages, in the first stage, the temperature of the polymerization is about 70°–90° C., and the time of the polymerization, identical or different to that in the first stage, is about 4–8 hours, preferably about 5–7 hours. The suspension polymerization according to the present invention can be carried out in a polymerization equipment well known in the art.

(2) Swelling and sulfonating the small resin beads

The small resin beads obtained by polymerization are subjected to the following treatments successively in a customary process for preparing sulfonated macroreticular cation exchange resin:

(a) Removing the paraffin wax and petroleum spirit by extraction:

The small beads are extracted by an extraction agent at a temperature of 0°–50° C., preferably at room temperature until no paraffin wax can be detected in the extract (which could be determined by refractive index measurement). The extraction agent is benzene, toluene, xylene, etc., in an amount of 1–100 fold, preferably 2–15 fold by volume of the small beads, and the extraction is preferably carried out in portions.

(b) Swelling and Sulfonating the resin beads:

The swelling agent and the sulfonating agent are added to the as-extracted small resin beads. The resin is sulfonated at 70°–95° C. for 4–8 hours while it is swollen. The temperature of the sulfonation is generally not more than the boiling point of the mixture of the swelling agent and the sulfonating agent depending upon the boiling point of the mixture of the swelling agent and the sulfonating agent.

The swelling agent used is selected from one of alcohols, acetone, phenol, acetone-phenol, dichloromethane, dichloroethane and other swelling agents well known in the art, the amount of which is about 30–70%, preferably about 40–60% by weight of the resin beads.

The sulfonating agent used is selected from one of sulfuric acid, sulfonic acid, methane-sulfonic acid, benzene sulfonic acid, p-toluene sulfonic acid and the like, which are the sulfonating agents well known in the art. The amount of the sulfonating agent is about 5–10 fold by weight of the small beads. The time for the sulfonation can be selected from 2–10 hours, and the sulfonation is preferably carried out in several stages, for example in two stages, and the temperature in the latter stage can be slightly higher than that in the former stage.

(C) Removing the residual swelling agent and the residual sulfonating agent:

After the sulfonation reaction is completed, the swelling agent can be removed by any suitable method, e.g. normal pressure distillation. The reaction solution is then gradually diluted with water and the sulfonated resin is washed to remove residual acid, until the effluent is neutral.

(d) Transforming the type of the resin:

The sulfonated resin can be transformed to alkali metal ionic type by a basic solution, or can be conviently transformed to H-type by an inorganic acid.

The commonly used basic solution is NaOH, KOH or the like, and the concentration of which may be 10–35% (by weight). The commonly used inorganic acid is hydrochloric acid, sulfuric acid or the like, preferably hydrochloric acid, the concentration of which is 2–10%, preferably 4–6% (by weight). Preferably, the resin is transformed to H-type which is practically used.

(3) Mercaptolizing the sulfonic acid type resin by mercaptolizing agent solution:

Thus prepared sulfonic acid type resin is mercaptolized according to the partial neutralization method disclosed in the prior art, in which alkyl mercaptoamine is used as the mercaptolizing agent.

The mercaptolizing agent solution comprises the following components %(by weight): 0.01%-saturated solution of alkylmercaptoamine organic or inorganic acid salt, having 1–7 carbon atoms; 0.01–50% of an acid selected from one of p-toluene sulfonic acid, formic acid, acetic acid, oxalic acid, hydrochloric acid, nitric acid and sulfuric acid; 0–98% of an organic swelling agent selected from one of alcohols having less than 5 carbon atoms, acetone, phenol, acetone-phelnol, dichloromethane and dichloroethane; and balance water.

The mercaptolizing agent solution can also be aqueous solution of alkyl mercaptoamine organic or inorganic acid salt, having 1–7 carbon atoms, which is formed by acidifying the above mentioned alkylmercaptoamine with an acid selected from one of p-toluene sulfonic acid, formic acid, acetic acid, oxalic acid, hydrochloric acid, nitric acid and sulfuric acid, the pH of which is <5 and the concentration of which is 0.005–0.5% by weight.

Preferably, the mercaptolization reaction is carried out by using the second mercaptolizing agent solution with lower concentration. The mercaptolization step can be carried out by statically impregnating the above treated resin with the mercaptolizing agent solution, or by passing the mercaptolizing agent solution through the resin once or multiple times. The former is preferred, because static impregnation has the following advantages: simplicity of equipment, convenience of operation and the resin being hardly broken and so on. The resin to be mercaptolized can be in dry state, or in swollen state in water or in the above-mentioned organic swelling solvent. The temperature of the mercaptolization is generally about 0°–90° C., preferably 0°–50° C., more preferably 25° C. or even lower. The time of the mercaptolization is generally about 24–96 hours, preferably about 48–72 hours. After the resin is mercaptolized, it is washed until the effluent is neutral, filtrated, and dried, optionally at reduced pressure, to obtain the product. The partial neutralization method for mercaptolizing sulfonated resin, which is described in Chinese Patent Application No. 91108831.8

BRIEF DESCRIPTION OF THE DRAWING

The accompanying drawing illustrates the schematic graph of the equipment used for the mercaptolization of the synthesized sulfonic acid type resin according to the present porcess, wherein, 1 is a reactor, 2 is a filter, 3 is a recycle pipe line, 4 is a storage vessel, and 5 is a pump.

The equipment used for the mercaptolization of the synthesized sulfonic acid type resin according to the present process can be the equipment described in Chinese Patent Application No. 91111615.X. This equipment is a closed recycle system, comprising a reactor, a filter, a storage vessel, a pump, and connection pipe lines. This equipment enables resin particulates to homogeneously suspended in solution, and to be in a slowly-floating and rolling state wherein the reactor can be a reaction kettle, a tubular reactor, a tower reactor, a reaction column, a vessle, a pot or a tank. The filter can be a device or a material selected from a ceramic filter, sintered glass, porous foam plastics, glass fiber, fiber plastics or its fabric, net and porous plate, which enables the fluid to pass freely, and prevents particulates from passing. In the reactor and the storage vessel, flow deflector, honeycomb duct and heating or cooling jacket can be installed. In the whole closed recycle system, the recycle direction, relative to the reactor, can be downwards, upwards, or transversed.

The catalyst provided by this invention has the above-mentioned special porous structure, thus has higher selectivity and activity than those of the catalyst in the prior art, they present catalyst is suitable for the condensation reaction between a phenol and a carbonyl compound to produce bisphenols, especially suitable for the condensation reaction of phenol and acetone to form bisphenol A.

For example, in the case of the molar ratio of phenol to acetone of 8, and at reaction temperature of 75° C., the catalyst provided by this invention can convert acetone to bisphenol A with a conversion of 58–74%, selectivity to bisphenol A of 99.2–99.9%, and color index of less than 10. The quality of the obtained product bisphenol A can reach polymer grade, common epoxy resin grade and insulated epoxy resin grade.

In the process for preparing the present catalyst, as a pore-forming agent with special composition is used, fundamental resin particulates with special porous structure are synthesized. Moreover, as a special mercaptolization process is used, the problem of the resin particulates being broken has been solved, which is usually encountered in many mercaptolization techniques in the prior art, and mercapto groups can be homogeneously distributed on surface of or inside the resin particulates. This perfect preparation process imparts excellent selectivity to resin catalyst.

EXAMPLE

Following examples will further illustrate this invention, but is not intended to limit the scope of this invention.

In examples, the porous structure of the catalyst was measured on Autopore 9220 type automatic porosimeter made in Micrometrics Corporation (US) by mercury intrusion method. The conversion of phenol and acetone to bisphenol A, and the selectivity to the target product bisphenol A were calculated as follows:

conversion $$C = \frac{C_{BP}(M_P \times R + M_A)}{M_{BP}} \times 100\%$$

in which $C_{BP}$ is the content of bisphenol A in the product; Mp is the molecular weight of phenol; R is the molar ratio of the starting phenol to acetone, $M_A$ is the molecular weight of acetone and $M_{BP}$ is the molecular weight of bisphenol A.

$$\text{selectivity } S = \frac{C_{BP}}{C_{BP} + C_2 + C_3 + C_4 + C_5} \times 100\%$$

in which, $C_{BP}$, $C_2$, $C_3$, $C_4$, $C_5$ are the contents of bisphenol A, 2,4-bisphenol A, triphenol, chroman, and other impurities in the reaction product, respectively.

The contents of all the components in the product were measured by HPLC. The color index of the product bisphenol A was measured by colorimetry on Pt-Co spectrophotometer.

Example 1

To a 5L three-neck flask was added 16.5 g of polyvinylalcohol (product from The Third Reagent Plant in Beijing) and 1600 ml of distilled water, then added 364.8 g of styrene (product from the Chemical Industry Corporation in Lanzhou), 36.5 g of divinylbenzene (product from the Chemical Industry Corporation in Lanzhou), 40.2 g of benzoyl peroxide (product from The Third Reagent Plant in Beijing), 17.7 g of refined paraffin wax (product from the Petroleum Chemical Corporation in Daqing) and 107.4 g of petroleum spirit (NY-200# product from the Petroleum Chemical Corporation in Daqing) respectively. The reaction was carried out with stirring at 82° C. for 6 hours, and at 90° C. for 6 hours, then the resin materials were removed, washed with water, and air dried, thus the resin particulates containing paraffin wax and petroleum spirit were obtained.

The above white beads was extracted three times with 1200 ml of benzene (product from the First Reagent Plant in Tianjing) in a Soxhlet's extractor until no paraffin was detected (by refractive index measurement) in the extract.

Using 200 g of dichloroethane (product from the First Regent Plant in Tianjing) as swelling agnet, and 2800 g of 94% by weight of sufuric acid solution (product from the Third Reagent Plant in Tianjing) as sulfonating agent, the reaction was carried out with stirring at 70° C. for 2 hours, and at 80° C. for another 6 hours. The temperature of the system was raised to 90° C., at which temperature the dischloroethane was distilled off, and the distillation was continuously carried out at 110°–120° C. at normal pressure for 2 hours, and under reduced pressure for 1 hour.

When the temperature of the system gradually dropped to below 35° C., the solution in the system was diluted gradually with water, and the resin was washed to remove the residual acid until the effluent was neutral. The resin was transformed into H-type with 5% aqueous solution of hydrochloric acid. 359 g of small white beads was obtained after drying.

To a mercaptolization reaction equipment was charged with 180 g of dry resin, 18 g of mercaptoethylamine hydrochlride (product from Medical Raw Material Plant in Changshou City), and 360 ml of water, then the pH of the solution was adjusted to 3 using hydrochloric acid.

The resin was impregnated at room temperature for 36 hours, then the resin was removed, and was washed with water until the effluent was neutral, filered, and dried at 80° C. for 6 hours, then dried in vaccum at 72° C. for 12 hours.

Example 2

The reaction was conducted using essentially the same materials, experimental procedures and operation conditions as in Example 1, except that the ratio of petroleum spirit to paraffin wax was different. The amount of petroleum spirit used in this example was 90.5 g, and the amount of paraffin wax was 29.2 g, the ratio thereof was 3.1.

Example 3

The reaction was conducted using essentially the same materials, experimental porcedures and operation conditions as those in Example 2, except that the concentration of the mercaptolizing agent, mercaptoethylamine hydrochloride, was lower, and was 0.3% (by weight). Correspondingly, longer impregnation time, 72 hours was used.

The relavent properties of the catalyst obtained in the above examples were analysed, with the results listed in the following Table 1.

TABLE 1

|  | Example 1 | Example 2 | Example 3 |
|---|---|---|---|
| The weight ratio of petroleum spirit to paraffin wax | 6.1 | 3.1 | 3.01 |
| Exchange capacity (meq/g dry resin) | 4.66 | 4.72 | 4.73 |
| The percetage ratio of the pore capacity of micropore area (%) | 51 | 78 | 65 |
| The ratio of the pore capacity of the micropore area to that of the transfer pass network | 0.25 | 1 | 1.1 |
| Mercaptolizing degree (%) | 16.95 | 17.2 | 16.8 |
| Number of the catalyst | A | B | C |

Example 4–6

The catalyst of the present invention was prepared in the equipment described in CN 911 11615XA.

The resin beads were prepared according to the processes described in Examples 1–3, and they were sulfonated and transformed.

The mercaptolization reaction was conducted in the equipment shown in FIG. 1, wherein the reactor is a tower reactor with an inner diameter of 40 mm and a height of 590 mm; the filter is a sintered porous glass filter; the recycle pipe line was a glass tube with an inner diameter of 8 mm, and the storage vessel is a glass lined kettle with a capacity of 10 liters. 500 g of the above-mentioned sulfonated resin was charged into the reactor, and 6L of an aqueous solution containing 20 g of mercaptoethylamine hydrochloride (pH=

1) which was acidified with p-toluene sulfonic acid (product from the Chemical Industry Plant in Beijing) was charged into the storage vessel. The aqueous solution of the mercaptolizing agent was pumped at a flow rate of 14 liter per hour by a pump at room temperature from the storage vessel via the filter into the bottom of the reactor, where it contacted with the resin. The effluent flowed out from the top of the reactor through filtration, then returned back into the storage vessel and recycled consecutively for 24 hours. After the recycle was over, the resin was washed until the effluent was neutral, filtered, and dried at 80° C. for 6 hours, and in vaccum at 72° C. for 12 hours.

The revalent properties of the above-mentioned catalysts was analysed, with the results listed in the following Table 2.

TABLE 2

|  | Example 4 | Example 5 | Example 6 |
|---|---|---|---|
| The weight ratio of petroleum spirit to paraffin wax | 6.1 | 3.1 | 3.01 |
| Exchange capacity (meq/g dry resin) | 4.66 | 4.72 | 4.73 |
| The percetage ratio of the pore capacity of micropore area (%) | 51 | 78 | 65 |
| The ratio of the pore capacity of the micropore area to that of the transfer pass network | 0.25 | 1 | 1.1 |
| Mercaptolizing degree (%) | 16.85 | 17.1 | 16.9 |
| Number of the catalyst | D | E | F |

Application Example 1–6

When used to prepare bisphenol A, the catalyst of the present invention possesses higher activity and selectivity with better color index of bisphnol A.

130 g of phenol (porduct from the First Reagent Plant in Tianjing) and 10 g of acetone (product from the Chemical Industry Plant in Beijing) were reacted with stirring in the presence of 20 g of the catalysts at 75° C. for 1 hour, the conversion of acetone to bisphenol A, the selectivity to bisphenol A and the color index of bisphenol A were measured, the results were listed in Table 3.

To illustrate the characterization of the present catalyst, another three prior catalysts without the porous structure of the present catalyst were measured in parallel under the same conditions, the results were also listed in Table 3.

We claim:

1. An ion-exchange resin, which comprises; a sulfonated styrene-divinylbenzene copolymer having pendant sulfonic acid groups, 10 to 30 percent of said sulfonic acid groups being ionically linked by ammonium sulfonate to alkylmercaptoamine groups containing 1 to 7 carbon atoms;

said resin having a porous structure with micropore area and transfer pass networks, the transfer pass network composed of main pass networks and branch pass networks, in non-swollen state, the pore size of the main pass network is $9 \times 10^3 - 38 \times 10^3$ nanometer and the pore size of the branch pass network is 20–150 nanometer, the pore size of the micropore area pass is 5–20 nanometer, wherein the pore capacity of the micropore pass with the pore size of 5–10.4 nm is more than 50% of the total pore capacity of the micropore area, and the ratio of the pore capacity of the micropore area to that of the transfer network area is 0.25–1.1; and an exchange capacity of 2.8–5.5 meq/g dry resin.

2. A process for the preparation of an ion exchange resin catalyst which comprises;

(1) suspension polymerizing styrene and divinylbenzene monomers to prepare white resin beads in the presence of a pore-forming agent, wherein the weight ratio of divinylbenzene to styrene is 5–25%:95–75%, the pore-forming agent is composed of a refined paraffin wax and petroleum spirit with the weight ratio of paraffin wax to petroleum spirit being 1:3–6.1;

(2) swelling and sulfonating the resin beads comprising
  a) removing the paraffin wax and petroleum spirit from the resin obtained by the above polymerization by using an extracting agent,
  b) swelling and sulfonating the tesin beads by using a swelling agent and a sulfonating agent,
  c) removing the residual swelling agent and the residual sulfonating agent, and
  d) reacting the swollen and sulfonated resin with an inorganic acid or an alkali metal salt; and (3) mercaptolizing the sulfonic acid resin by using a mercaptolizing agent solution, washing the resin, drying and obtaining the catalyst product.

3. The process according to claim 2, wherein the suspension polymerization is carried out to a cross-linking degree of 3–15%.

4. The process according to claim 3, wherein the suspension polymerization is carried out to a cross-linking degree of 7–12%.

TABLE 3

| Catalyst | A | B | C | D | E | F | Control 1 | Control 2 | Control 3 |
|---|---|---|---|---|---|---|---|---|---|
| Percent ratio of the pore capacity of micropore pass to the total pore capacity of micropore area | 51 | 78 | 65 | 51 | 78 | 65 | 32 | 48 | 15 |
| Ratio of the pore capacity of micropore area to the pore capacity of transfer pass network | 0.25 | 1 | 1.1 | 0.25 | 1 | 1.1 | 0.12 | 0.14 | 1.8 |
| Conversion of acetone to bisphenol A (% wt) | 58.6 | 63.9 | 60.2 | 73.7 | 74.1 | 73.3 | 49.08 | 53 | 43 |
| Selectivity of bisphenol A (% wt) | 99.25 | 99.6 | 99.4 | 99.3 | 99.7 | 99.5 | 96.1 | 99.23 | 92.5 |
| The color index of bisphenol A | 9.8 | 8.4 | 8.9 | 9 | 8 | 8.5 | 40 | 22 | 50 |

5. The process according to claim 1, wherein the mercaptolization is at ambient temperature by statically impregnating the resin with a mercaptolizing agent solution.

6. The process according to claim 5, wherein the mercaptolizing agent solution has the following components (% by weight):

0.0%-saturated solution of alkyl mercaptoamine organic or inorganic acid salt having 1–7 carbon atoms; 0.01–50% of an acid selected from one of p-toluene sulfonic acid, formic acid, acetic acid, oxalic acid, hydrochloric acid, nitric acid and sulfuric acid; 0–98% of an organic swelling agent selected from one of alcohols having less than 5 carbon atoms, acetone, phenol, acetone-phenol, dischloromethane and dichloroethane; and balance water.

7. The process according to claim 5, wherein the mercaptolizing agent solution is an aqueous solution of alkyl mercaptoamine organic or inorganic acid salt having 1–7 carbon atoms, which is formed by acidifying the alkylmercaptoamine with an acid selected for the group consisting of one of p=toluene sulfonic acid; formic acid, acetic acid, oxalic acid, hydrochloric acid, nitric acid and sulfuric acid, the pH of which is <5, and the concentration of which is 0.005–0.5% by weight.

8. The process according to claim 7, wherein the mercaptolizing is in a closed recycle equipment comprising a reactor, a filter, a storage vessel, a pump, and connection pipe lines.

9. The process according to claim 8, wherein the reactor is a reaction kettle, a tubular reactor, a tower reactor, a reaction column, a vessel, a pot or a tank.

10. The process according to claim 8, wherein the filter is a material selected from a ceramic filter, sintered glass, porous foam plastics, glass fiber, fibreplastics or its fabric, net and porous plate, which enables fluid to pass freely and prevents particulates from passing.

11. The process according to claim 8, wherein a flow deflector, a honeycomb duct or a jacket is installed in the reactor.

12. The process according to claim 5, wherein the resin to be mercaptolized is in dry state or in swellon state in water or in an organic swelling agent.

* * * * *

UNITED STATES PATENT AND TRADEMARK OFFICE
CERTIFICATE OF CORRECTION

PATENT NO. : 5,759,942

DATED : June 2, 1998

INVENTOR(S) : Qui Tan, Zuguan Jin, Hongshou Jiang, Zongzhang Liu and Binjun He

It is certified that error appears in the above-identified patent and that said Letters Patent is hereby corrected as shown below:

Col. 1, line 18; "styrene-divinylbenezene" should read
-- styrene-divinylbenzene --

Col. 1, line 19; "benezene-" should read -- benzene- --

Col. 2, line 12; "styrene-divinylbenezene" should read
-- styrene-divinylbenzene --

Col. 2, line 33; "divinylbenezene" should read
-- divinylbenzene --

Col. 2, line 35; "divinylbenezene" should read
-- divinylbenzene --

Col. 2, line 48; after "polymerization," insert
-- is about 4-8 hours, preferably about 5-7 hours; in the second stage, the temperature of the polymerization is about 80-95°C, and the time of the polymerization --

UNITED STATES PATENT AND TRADEMARK OFFICE
CERTIFICATE OF CORRECTION

PATENT NO. : 5,759,942
DATED : June 2, 1998
INVENTOR(S) : Qui Tan, Zuguan Jin, Hongshou Jiang, Zongzhang Liu and Binjun He It is certified that error appears in the above-identified patent and that said Letters Patent is hereby corrected as shown below:

Col. 4, line 34; "suspended" should read -- suspend --
Col. 4, line 58; "99.2-99.9%" should read -- 99.2-99.7% --
Col. 4, line 49; "they" should read -- the --
Col. 6, line 6; "359" should read -- 395 --
Col. 9, line 13; "dischloromethane" should read -- dichloromethane --
Col. 9, line 20; "p=toluene" should read -- p-toluene --

Signed and Sealed this

Twentieth Day of October, 1998

Attest:

BRUCE LEHMAN

*Attesting Officer*    *Commissioner of Patents and Trademarks*